United States Patent
Zhang et al.

(10) Patent No.: US 10,787,451 B2
(45) Date of Patent: Sep. 29, 2020

(54) CRYSTALLINE FORM OF GNRH RECEPTOR ANTAGONIST AND PREPARATION METHOD THEREFOR

(71) Applicants: Jiangsu Hengrui Medicine Co., Ltd., Lianyungang, Jiangsu (CN); Suncadia Pharmaceuticals Co., Ltd., Chengdu, Sichuan (CN)

(72) Inventors: Quanliang Zhang, Jiangsu (CN); Junlei Jia, Jiangsu (CN); Lin Bian, Jiangsu (CN); Xiaohui Gao, Jiangsu (CN)

(73) Assignees: Jiangsu Hengrui Medicine Co., Ltd., Lianyungang, Jiangsu (CN); Suncadia Pharmaceuticals Co., Ltd., Chengdu, Sichuan (CN)

( * ) Notice: Subject to any disclaimer, the term of this patent is extended or adjusted under 35 U.S.C. 154(b) by 0 days.

(21) Appl. No.: 16/348,932

(22) PCT Filed: Nov. 13, 2017

(86) PCT No.: PCT/CN2017/110685
§ 371 (c)(1),
(2) Date: May 10, 2019

(87) PCT Pub. No.: WO2018/086608
PCT Pub. Date: May 17, 2018

(65) Prior Publication Data
US 2019/0276455 A1    Sep. 12, 2019

(30) Foreign Application Priority Data
Nov. 14, 2016 (CN) .......................... 2016 1 0999743

(51) Int. Cl.
C07D 473/28 (2006.01)
C07D 487/04 (2006.01)
A61K 31/519 (2006.01)
A61P 15/00 (2006.01)

(52) U.S. Cl.
CPC .......... *C07D 473/28* (2013.01); *A61K 31/519* (2013.01); *A61P 15/00* (2018.01); *C07D 487/04* (2013.01); *C07B 2200/13* (2013.01)

(58) Field of Classification Search
CPC ... A61K 31/519; A61P 15/00; C07B 2200/13; C07D 473/28; C07D 487/04
See application file for complete search history.

(56) References Cited

U.S. PATENT DOCUMENTS

2016/0264578 A1* 9/2016 Lu .................. C07D 487/04

FOREIGN PATENT DOCUMENTS

| CN | 104884457 A | 9/2015 |
|---|---|---|
| WO | 2006096785 A1 | 9/2006 |
| WO | 2010026993 A1 | 3/2010 |
| WO | 2011076687 A1 | 6/2011 |
| WO | 2012175514 A1 | 12/2012 |
| WO | 2015062391 A1 | 5/2015 |

OTHER PUBLICATIONS

Int'l Search Report dated Feb. 24, 2018 in Int'l Application No. PCT/CN2017/110685.

* cited by examiner

*Primary Examiner* — Erich A Leeser
(74) *Attorney, Agent, or Firm* — Ice Miller LLP

(57) ABSTRACT

Provided are a crystalline form of a GnRH receptor antagonist and a preparation method therefor. Specifically, provided are a crystalline form I of 1-(4-(7-(2,6-difluorobenzyl)-3-((dimethylamino)methyl)-5-(6-methoxypyridazin-3-yl)-4,6-dicarbonyl-4,5,6,7-tetrahydro-2H-pyrazolo[3,4-d]pyrimidin-2-yl)phenyl)-3-methoxy urea (a compound of formula I) and a preparation method, the use of same in a pharmaceutical composition and the use of the crystalline form I and the composition in the preparation of a drug for treating diseases associated with a GnRH receptor antagonist.

20 Claims, 10 Drawing Sheets

CRYSTALLINE FORM OF GNRH RECEPTOR ANTAGONIST AND PREPARATION METHOD THEREFOR

CROSS-REFERENCE TO RELATED APPLICATION

This application is a Section 371 of International Application No. PCT/CN2017/110685, filed Nov. 13, 2017, which was published in the Chinese language on May 17, 2018 under International Publication No. WO 2018/086608 A1, which claims priority under 35 U.S.C. § 119(b) to Chinese Application No. 201610999743.3, filed Nov. 14, 2016, and the disclosures of which are incorporated herein by reference.

FIELD OF THE INVENTION

The present invention relates to crystal form I of 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea and a preparation method thereof, use of the same in a pharmaceutical composition, and use of the crystal form I and the composition in the preparation of a medicament for the treatment and/or prevention of a disease associated with GnRH receptor antagonist.

BACKGROUND OF THE INVENTION

Endometriosis is a common estrogen-dependent gynecological disease, which often occurs in women of childbearing age, though the action mechanism of which is unclear. At present, endometriosis is mainly diagnosed by laparoscopy, and treated by surgery, or controlled by taking contraceptive, GnRH receptor agonists or progestogen to reduce estrogen levels in the body.

Gonadotropin-releasing hormone (GnRH), also known as luteinizing hormone-releasing hormone (LHRH), is a central regulation factor of the endocrine and reproductive system. The secretion and release of gonadotropin such as luteinizing hormone (LH) and follicle-stimulating hormone (FSH) can regulate the normal development of ovary and corpus luteum, and play an important role in the hypothalamus-pituitary-gonadal axis. GnRH receptor plays its regulating role by coupling with G protein that activates the second messenger system of phosphatidylinositol and calcium. LH regulates the production of sex steroids, while FSH regulates male spermatogenesis and female follicular development.

LH and FSH are released into the circulation, and bind to receptors on the specific cells of ovaries or testes to stimulate steroid production. Diseases such as endometriosis, uterine leiomyoma and prostate cancer are aggravated in the presence of sex steroids, and long-acting peptide GnRH receptor agonists and antagonists need to be administered for therapeutic control.

There are many issues to be solved for peptide compounds, including oral absorption, dosage form, dose volume, drug stability, sustained action, and metabolic stability and the like. The primary reason why small molecule GnRH receptor antagonist therapy is superior to the existing peptide-based therapy is that small molecule GnRH receptor antagonists can be directly administered orally, which is convenient and efficient.

Indirect tumor inhibition mechanism mediated by GnRH receptor agonists lies in reducing pituitary gonadotropins (FSH, LH) by long-term action on the hypothalamic-pituitary-gonadal axis, thereby reducing the secretion of sex hormones and indirectly inhibiting the growth of tumor cells. GnRH receptor antagonists directly inhibit the release of pituitary gonadotropins, thereby inhibiting the growth of tumor cells.

A series of patent applications currently disclosing small molecule GnRH receptor antagonists include WO2006096785, WO2010026993, WO2011076687 and WO2012175514. Small molecule GnRH receptor antagonists have good application prospects as drugs in the pharmaceutical industry. The applicant provides a high-efficiency and low-toxic GnRH receptor antagonist with a novel structure, which has excellent efficacy and effect, and can effectively treat an endocrine and reproductive system disease in the patent application WO2015062391A1 (publication date 7 May 2015). Its chemical name is 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea, and the structure is shown below

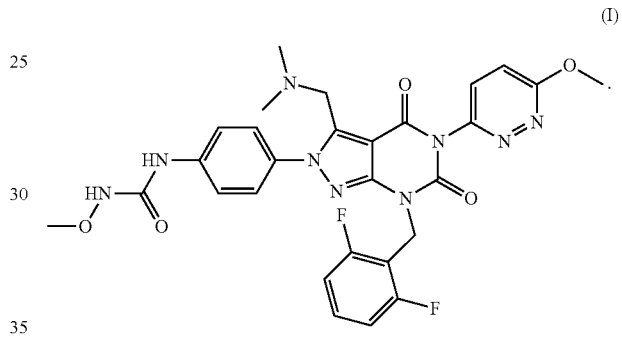

(I)

The crystal structure of a pharmaceutically active ingredient often affects the chemical stability of the drug. Differences in crystal form, preparation method and storage condition may lead to changes in the crystal structure of the compound, and sometimes accompanying production of other crystal forms. In general, an amorphous drug product does not have a regular crystal structure, and often has other defects such as poor product stability, difficult filtration, easy agglomeration, and poor liquidity, which often lead to difficulties in production amplification. The stability of existing crystal forms needs to be improved. Therefore, it is necessary to improve the various properties of the above compound. There is a need to find a novel crystal form with high purity and good chemical stability.

SUMMARY OF THE INVENTION

The technical problem to be solved by the present invention is to provide crystal form I of 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea (as shown in formula (I)). The crystal form has good stability and can be better applied in clinical practice, and the crystallization solvent used is low in toxicity and low in residue.

The technical solution of the present invention is as follows:

The present invention provides crystal form I of a compound of formula (I), characterized in that: the crystal form I has an X-ray powder diffraction spectrum, which is obtained by using Cu-Kα radiation and represented by diffraction angle 2θ angle, in which there are characteristic peaks at 5.56, 9.15, 9.79, 11.08, 19.59, 20.25 and 22.16, wherein the error range of 2θ angle of each characteristic peak is ±0.2,

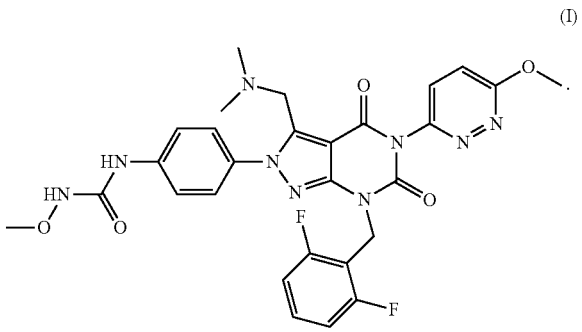

In a preferred embodiment of the present invention, the present invention provides crystal form I of the compound of formula (I), characterized in that: the crystal form I has an X-ray powder diffraction spectrum, which is obtained by using Cu-Kα radiation and represented by diffraction angle 2θ angle, in which there are characteristic peaks at 5.56, 9.15, 9.79, 10.29, 11.08, 14.21, 16.61, 19.59, 20.25, 22.16 and 25.69, wherein the error range of 2θ angle of each characteristic peak is ±0.2.

In a preferred embodiment of the present invention, the present invention provides crystal form I of the compound of formula (I), characterized in that: the crystal form I has an X-ray powder diffraction spectrum, which is obtained by using Cu-Kα radiation and represented by diffraction angle 2θ angle, in which there are characteristic peaks at 5.22, 5.56, 9.15, 9.79, 10.29, 11.08, 13.38, 13.81, 14.21, 14.89, 16.61, 17.19, 18.47, 19.59, 20.25, 22.16, 23.32, 24.67, 25.69, 26.72, 28.73, 29.38, 31.78, 34.02 and 36.95, wherein the error range of 2θ angle of each characteristic peak is ±0.2.

In a preferred embodiment of the present invention, the present invention provides crystal form I of the compound of formula (I), characterized in that: the melting endothermic peak value of differential scanning calorimetry (DSC) spectrum is from 160° C. to 175° C., preferably from 165° C. to 170° C., and more preferably 168.17° C.

In a preferred embodiment of the present invention, the present invention further provides a method for preparing the crystal form I of the compound of formula (I), comprising the following steps of:

(1) method I, dissolving the compound of formula (I) in an organic solvent to precipitate a crystal, filtering, washing and drying the crystal to obtain the desired crystal form I, wherein the organic solvent is selected from the group consisting of an alcohol, ketone, ester, ether, a mixed solvent of an ether and an alcohol, and a mixed solvent of a ketone and water, the alcohol solvent is selected from the group consisting of methanol, ethanol and isopropanol, the ketone solvent is selected from acetone, the ester solvent is selected from ethyl acetate, the ether solvent is selected from tetrahydrofuran, the mixed solvent of the ether and the alcohol is selected from the group consisting of tetrahydrofuran/ethanol and tetrahydrofuran/isopropanol, the mixed solvent of a ketone and water is selected from acetone/water, the ratio of the alcohol to the ether in the mixed solvent of the alcohol and the ether is from 0.1:1 to 1:0.1, preferably tetrahydrofuran/ethanol=1:1 or tetrahydrofuran/isopropanol=1:1, the ratio of the ketone to water in the mixed solvent of the ketone and water is from 0.1:1 to 1:0.1, and preferably acetone/water=5:1; or (2) method II, adding the compound of formula (I) into an organic solvent, pulping the mixture, filtering, washing and drying a crystal to obtain the desired crystal form I, wherein the organic solvent is selected from the group consisting of an alcohol, ketone, ester, ether, a mixed solvent of an ether and an alcohol, and a mixed solvent of a ketone and water, the alcohol solvent is selected from the group consisting of methanol, ethanol and isopropanol, the ketone solvent is selected from acetone, the ester solvent is selected from ethyl acetate, the ether solvent is selected from tetrahydrofuran, the mixed solvent of the ether and the alcohol is selected from the group consisting of tetrahydrofuran/ethanol and tetrahydrofuran/isopropanol, the mixed solvent of the ketone and water is selected from acetone/water, the ratio of the alcohol to the ether in the mixed solvent of the alcohol and the ether is from 0.1:1 to 1:0.1, preferably tetrahydrofuran/ethanol=1:1 or tetrahydrofuran/isopropanol=1:1, the ratio of the ketone to water in the mixed solvent of the ketone and water is from 0.1:1 to 1:0.1, preferably acetone/water=1:1, the temperature for pulping is from room temperature to solvent boiling point temperature, the room temperature is preferably from 15 to 30° C., and more preferably 25° C.

The present invention further relates to a pharmaceutical composition of the crystal form I of the compound of formula (I), characterized by comprising one or more pharmaceutically acceptable carriers, diluents or excipients.

The present invention further relates to use of the crystal form I of the compound of formula (I) or the pharmaceutical composition of the crystal form I in the preparation of a medicament for the treatment and/or prevention of a disease associated with GnRH receptor antagonist, wherein the disease is selected from the group consisting of an endocrine and reproductive system disease.

The resulting crystal form I of the compound of formula (I) is determined by X-ray powder diffraction spectrum (XRPD) and differential scanning calorimetry (DSC). Meanwhile, the residual solvent in the resulting crystal is also determined.

The crystal form I of the compound of formula (I) prepared according to the method of the present invention does not contain or contains only a relatively low content of residual solvent, which meets the requirement of the National Pharmacopoeia concerning the limitation of the residual solvent of drug products. Therefore, the crystal of the present invention is suitable for use as pharmaceutical active ingredient.

The recrystallization method is not particularly limited, and can be carried out by a conventional recrystallization process. For example, the material, i.e., the compound of formula (I), can be dissolved in an organic solvent under heating, and then the solution is cooled slowly to precipitate a crystal. After the completion of crystallization, the desired crystal can be obtained via filtering and drying.

The crystallization method of the present invention includes room temperature crystallization, cooling crystallization and the like.

The starting material used in the method for preparing the crystal form of the present invention can be the compound of formula (I) in any form, and the specific forms include, but are not limited to, amorphous form, arbitrary crystal forms and the like.

Preferred Embodiment

In the description and claims of the present application, unless otherwise indicated, the scientific and technical terms used herein have the meanings generally understood by a person skilled in the art. However, in order to understand the present invention better, definitions and explanations of some relevant terms are provided below. In addition, when the definitions and explanations of the terms provided in the present application are inconsistent with the meanings generally understood by a person skilled in the art, the definitions and explanations of the terms provided in the present application shall prevail.

The term "pulping" used in the present invention refers to a method of purification which utilizes the property that the solubility of a compound is poor in a solvent, while the solubility of impurities is good in the solvent. Pulping purification can remove color, change crystal form or remove small amounts of impurities.

The term "$C_{1-6}$ alkyl" used in the present invention refers to a straight or branched alkyl containing 1-6 carbon atoms, and its specific examples include but are not limited to: methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc.

The term "hydroxy" used in the present invention refers to —OH group.

The term "ketone solvent" used in the present invention refers to a compound in which a carbonyl group (—C(O)—) is bonded to two hydrocarbon groups. Ketones can be classified into aliphatic ketones, alicyclic ketones, aromatic ketones, saturated ketones, and unsaturated ketones, depending on the hydrocarbon group in the molecule. Its specific examples include but are not limited to: acetone, methyl butanone or methyl isobutyl ketone.

The term "ester solvent" used in the present invention refers to a combination of a lower organic acid having 1 to 4 carbon atoms and a lower alcohol having 1 to 6 carbon atoms. Its specific examples include but are not limited to: ethyl acetate, isopropyl acetate or butyl acetate.

The term "ether solvent" used in the present invention refers to a chain compound or a cyclic compound having an ether bond —O— and having 1 to 10 carbon atoms. Its specific examples include but are not limited to: propylene glycol methyl ether, tetrahydrofuran or 1,4-dioxane.

The term "alcohol solvent" used in the present invention refers to a group derived from the substitution of one or more hydrogen atoms on the "$C_{1-6}$ alkyl" by one or more "hydroxys", wherein the "hydroxy" and "$C_{1-6}$ alkyl" are as defined above. Its specific examples include but are not limited to: methanol, ethanol, propanol or 2-propanol.

The term "mixed solvent" used in the present invention refers to a solvent obtained by mixing one or more different kinds of organic solvents in a certain ratio, or a solvent obtained by mixing an organic solvent and water in a certain ratio. The ratio is volume ratio, which is from 0.1:1 to 1:0.1, and preferably 1:1 or 5:1. The mixed solvent is preferably a mixed solvent of an alcohol and an ether, a mixed solvent of an alcohol and water, or a mixed solvent of a ketone and water.

The term "X-ray powder diffraction spectrum or XRPD" used in the present invention refers to an X-ray powder diffraction spectrum that is obtained according to the Bragg formula $2d \sin \theta = n\lambda$ (where $\lambda$ is the wavelength of the X-ray, $\lambda=1.54056$ Å, the order of diffraction n is any positive integer, generally taking the first-order diffraction peak, n=1), when the X-ray is incident on a certain atomic plane of a crystal or a partial crystal sample having a d-lattice plane spacing at a glancing angle $\theta$ (the complementary angle of incidence angle, also called the Bragg angle), the Bragg equation can be satisfied.

The term "differential scanning calorimetry or DSC" used in the present invention means to measure the temperature difference and heat flow difference between the sample and the reference during the heating or constant temperature process of the sample, to characterize all physical and chemical changes associated with the thermal effect, and to obtain phase change information of the sample.

The term "2θ or 2θ angle" used in the present invention refers to the diffraction angle, θ is the Bragg angle, and the unit of which is ° or degree. The error range of 2θ is from ±0.1 to ±0.5, preferably from ±0.1 to ±0.3, and more preferably ±0.2.

The term "interplanar spacing or interplanar distance (d value)" used in the present invention means that the space lattice selects three unit vectors a, b, c, wherein each of them connects two adjacent lattice dots, and the three vectors divide the lattice into juxtaposed parallel juxtagonal units, called the interplanar spacing. The space lattice is divided according to the determined parallelepiped unit lines to obtain a set of linear grids, which is called a space lattice or a lattice. The lattice reflects the periodicity of the crystal structure with geometric points and lines. Different crystal planes have different interplanar spacings (i.e., distance between two adjacent parallel crystal planes); the unit is Å or angstrom.

The present invention further relates to a pharmaceutical composition comprising the crystal form I of the compound of formula (I) and optionally one or more pharmaceutically acceptable carriers and/or diluents. The pharmaceutical composition can be formulated into any pharmaceutically acceptable dosage forms. For example, the crystal form I or pharmaceutical formulation of the present invention can be formulated into tablets, capsules, pills, granules, solutions, suspensions, syrups, injections (including injection solution, sterile powder for injection, and concentrated solution for injection), suppositories, inhalants or sprays.

In addition, the pharmaceutical composition of the present invention can also be administrated to a patient or subject in need of such treatment by any suitable administration mode, such as oral, parenteral, rectal, intrapulmonary or topical administration. For oral administration, the pharmaceutical composition can be formulated into an oral formulation, for example, an oral solid formulation such as a tablet, capsule, pill, granule, and the like; or an oral liquid formulation such as an oral solution, oral suspension, syrup, and the like. When formulated into an oral formulation, the pharmaceutical composition can further comprise a suitable filler, binder, disintegrator, lubricant, and the like. For parenteral administration, the pharmaceutical composition can be formulated into an injection formulation including an injection solution, sterile powder for injection and concentrated solution for injection. When formulated into an injection formulation, the pharmaceutical composition can be produced by a conventional method in current pharmaceutical industry. When an injection formulation is formulated, an additional agent may not be added to the pharmaceutical preparation, or a suitable additional agent may be added depending on the nature of the medicament. For rectal administration, the pharmaceutical formulation can be formulated into a suppository and the like. For intrapulmonary administration, the pharmaceutical formulation can be formulated into an inhalant or spray and the like. In certain preferred embodiments, the crystal form I of the present invention is present in the pharmaceutical composition or medicament in a therapeutically and/or prophylactically effective amount. In certain preferred embodiments, the crystal form I of the present invention is present in the pharmaceutical composition or medicament in unit dose.

The crystal form I of the compound of formula (I) of the present invention can be used to prepare a medicament for the treatment and/or prevention of a disease associated with GnRH receptor antagonist. Therefore, the present application further relates to use of the crystal form I of the compound of formula (I) of the present invention in the preparation of a medicament for the treatment and/or prevention of a disease associated with GnRH receptor antagonist in a subject. Moreover, the present application further relates to a method for inhibiting a disease associated with GnRH receptor antagonist, comprising administering a therapeutically and/or prophylactically effective amount of the crystal form I of the compound of formula (I) of the present invention or the pharmaceutical composition of the present invention to a subject in need thereof.

In certain preferred embodiments, the disease is a disease associated with GnRH receptor antagonist: an endocrine and reproductive system disease.

Advantageous Effects of the Present Invention

Compared with the prior art, the technical solution of the present invention has the following advantages:

(1) The crystal form I of the compound of formula (I) of the present invention does not contain or contains only a relatively low content of residual solvent, which meets the requirement of the National Pharmacopoeia concerning the limitation of the residual solvent of drug products. Therefore, the crystal of the present invention is suitable for use as pharmaceutical active ingredient.

(2) The experimental results show that the crystal form I of the compound of formula (I) prepared according to present invention has high purity, and is unchanged under the conditions of lighting, high temperature and high humidity as determined by XRPD, and is stable. The HPLC purity change is slight, and the chemical stability is high. The crystal form I of the compound of formula (I) prepared by the technical solution of the present invention can meet the production, transportation and storage requirements of drug products. Its preparation process is stable, repeatable and controllable, and can be adapted to industrial production.

DETAILED DESCRIPTION OF THE INVENTION

The present invention will be illustrated by the following examples in detail. The examples of the present invention are merely intended to describe the technical solution of the present invention, and should not be considered as limiting the spirit and scope of the present invention.

Test conditions for the instruments used in the experiments:

1. Differential Scanning Calorimeter, DSC
Instrument type: Mettler Toledo DSC 1 STAR$^e$ System
Purging gas: Nitrogen
Heating rate: 10.0° C./min
Temperature range: 40-300° C.

2. X-Ray Powder Diffraction, XRPD
Instrument type: Bruker D8 Focus X-ray powder diffractometer
Ray: monochromatic Cu-Kα ray (λ=1.5406)
Scanning mode: θ/2θ, Scanning range: 2-40°
Voltage: 40 kV, Electric current: 40 mA Example 1

The crude 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea (300 mg, 0.49 mmol) (prepared according to the method of Example 11 of WO2015062391A1) was added to a reaction flask, a mixed solvent of acetone/water (5 mL, V:V=5:1) was added, and the resulting mixture was heated to reflux. The heating was stopped when the solid was dissolved completely, and the solution was cooled to precipitate a crystal. The mixture was filtered and dried under vacuum to obtain 212 mg of a solid. The crystal sample was determined by XRPD, and there are characteristic peaks at diffraction angle 2θ of 5.19 (17.02), 5.48 (16.10), 9.08 (9.73), 9.73 (9.08), 10.24 (8.63), 11.01 (8.03), 13.80 (6.41), 14.13 (6.26), 14.82 (5.97), 15.35 (5.77), 16.56 (5.35), 18.31 (4.84), 18.65 (4.75), 19.50 (4.55), 20.18 (4.40), 22.07 (4.03), 23.26 (3.82), 24.59 (3.62), 25.61 (3.48), 26.66 (3.34), 28.69 (3.11), 29.30 (3.05), 33.96 (2.64) and 36.91 (2.43). The crystal form was defined as crystal form I.

Example 2

Figure 1:
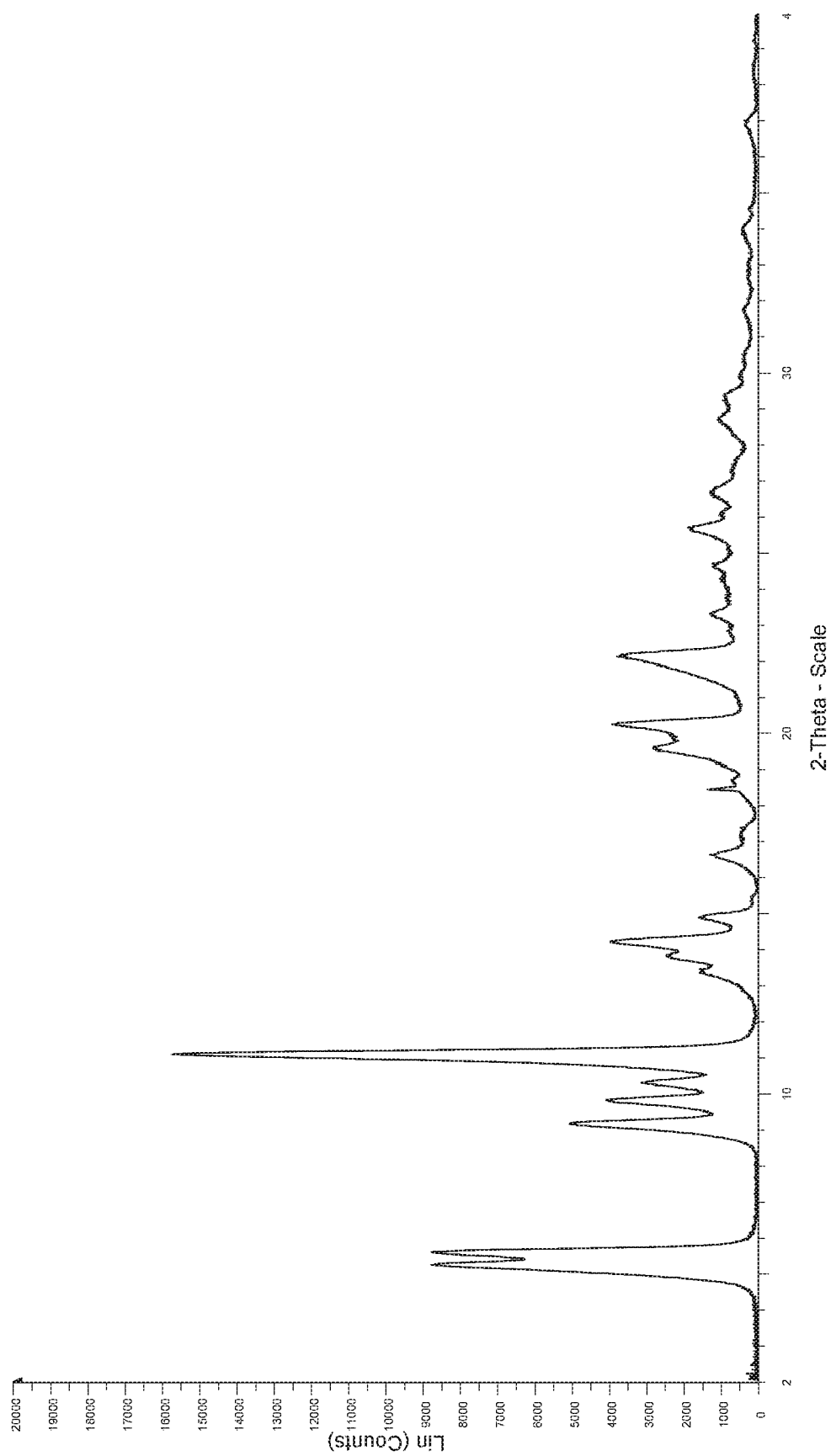
FIG. 1 shows the XRPD spectrum of crystal form I of the compound of formula (I).
Figure 2:
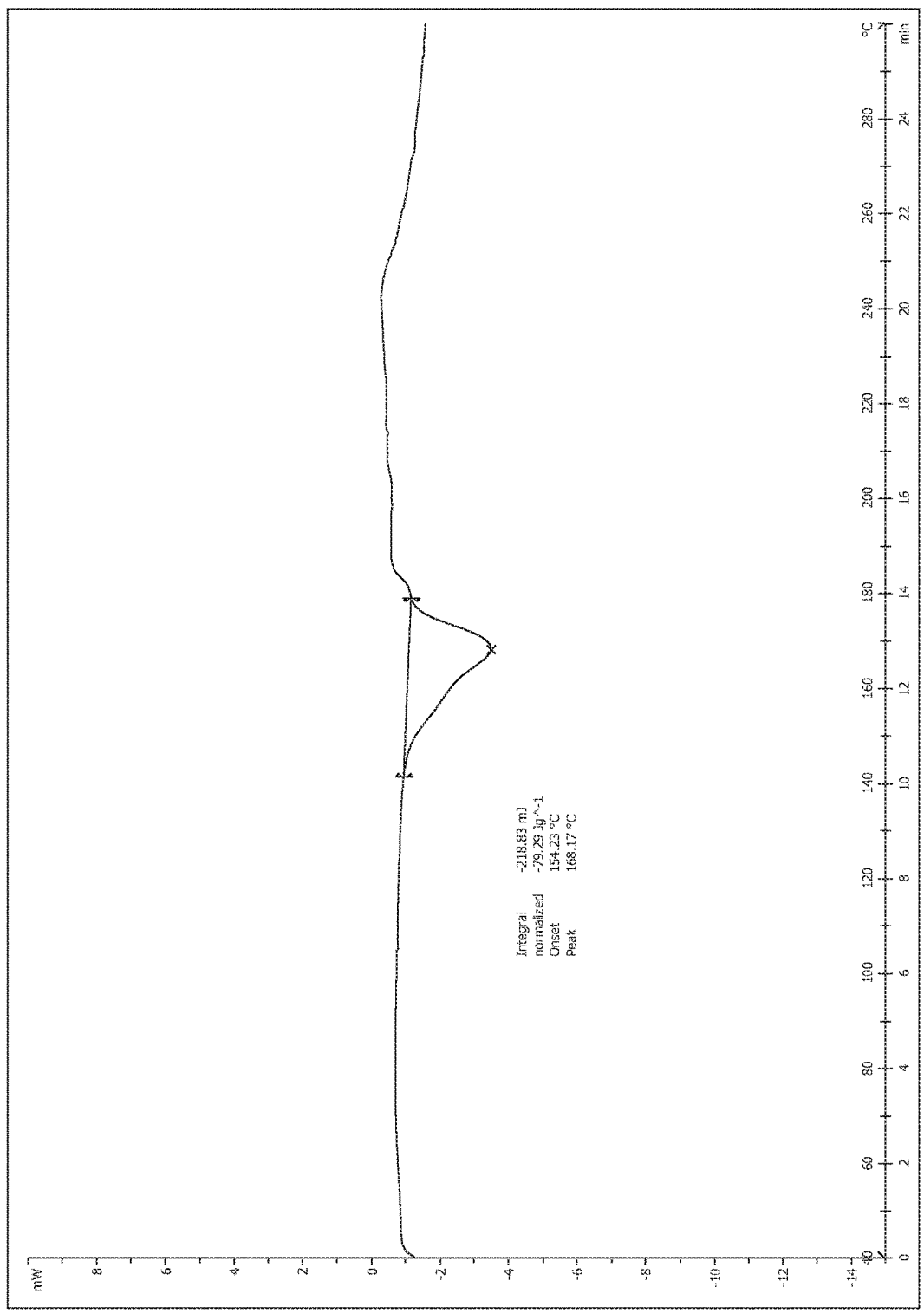
FIG. 2 shows the DSC spectrum of crystal form I of the compound of formula (I).
Figure 3:
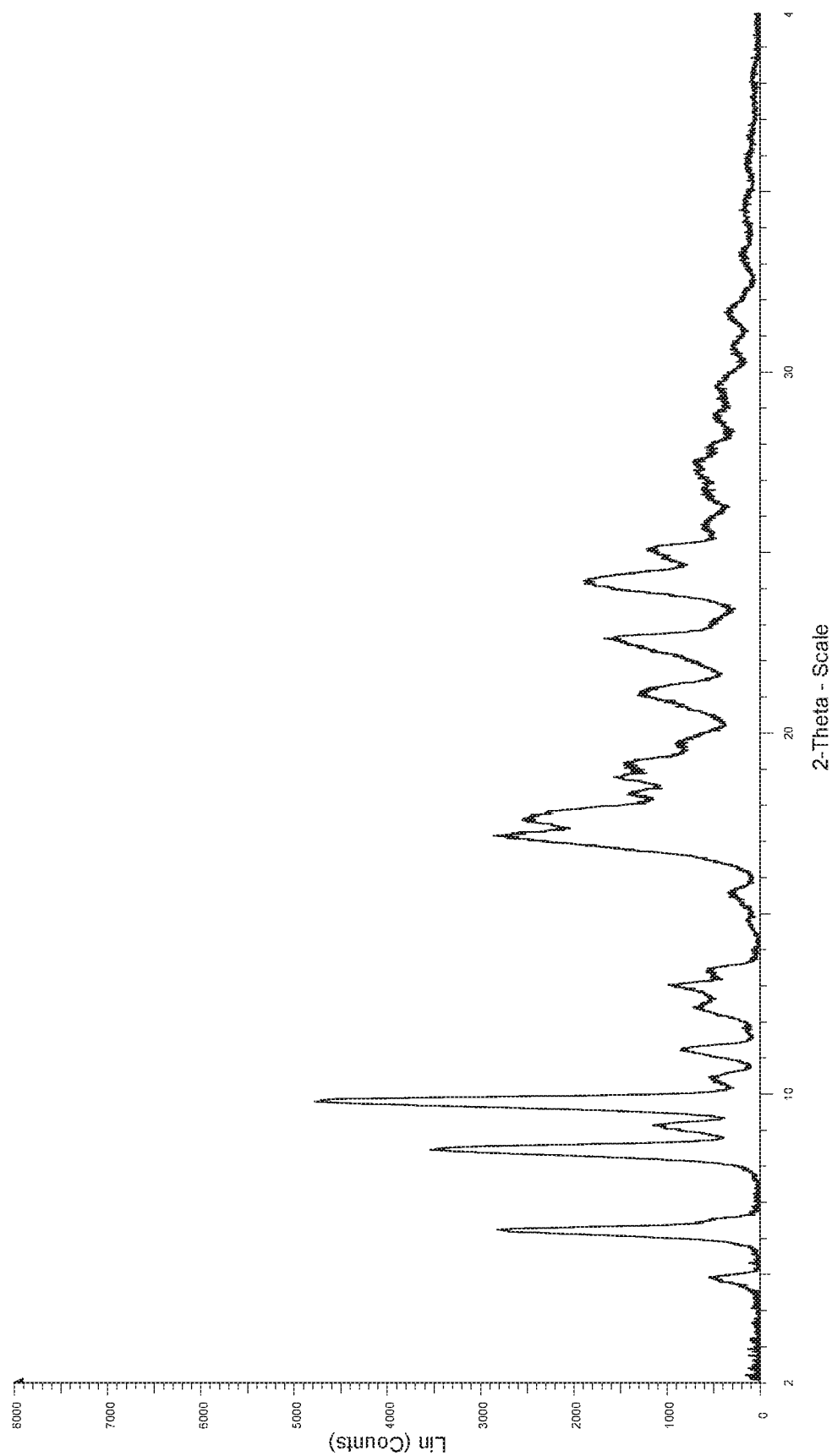
FIG. 3 shows the XRPD spectrum of crystal form A of the compound of formula (I).
Figure 4:
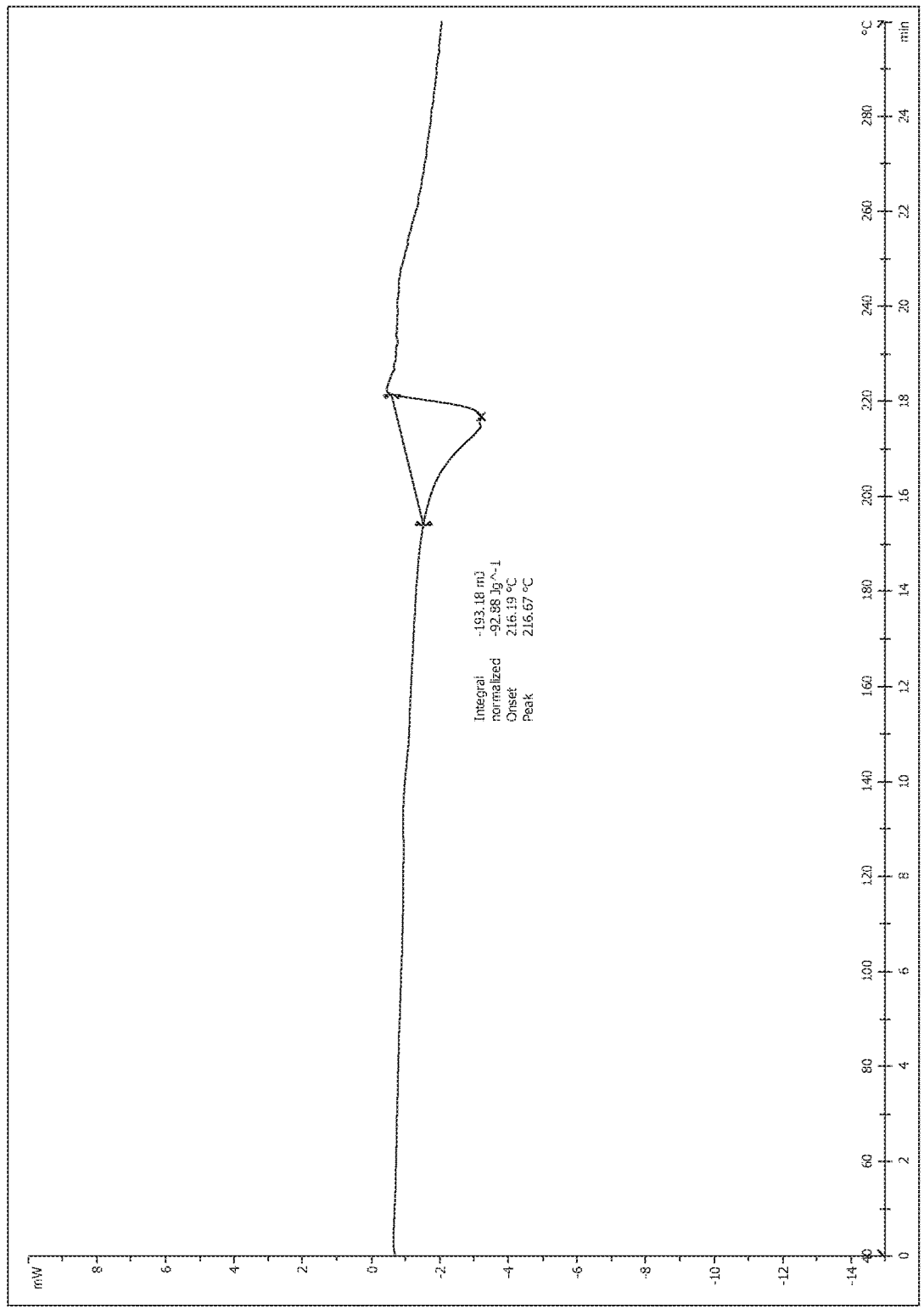
FIG. 4 shows the DSC spectrum of crystal form A of the compound of formula (I).
Figure 5:
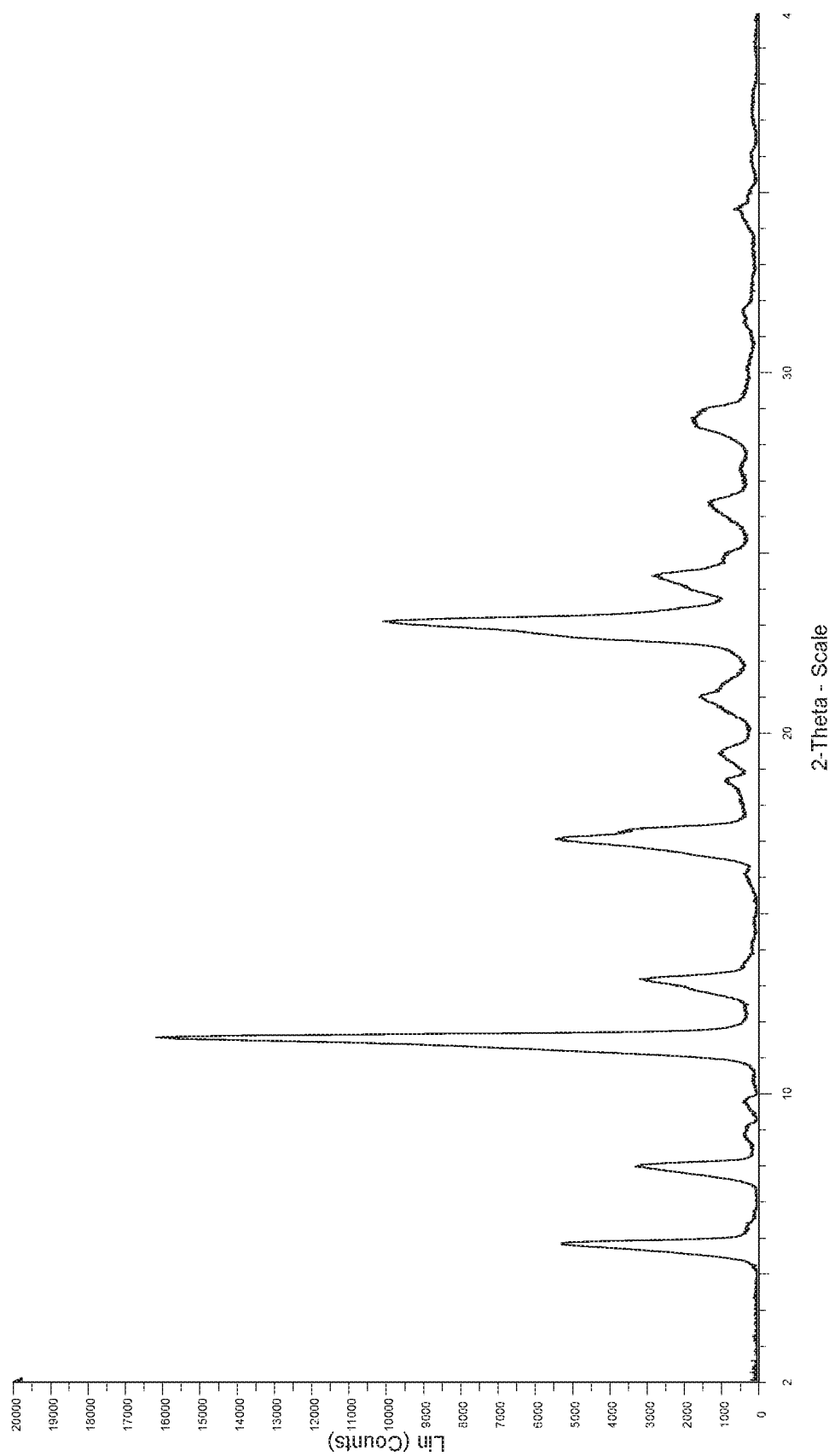
FIG. 5 shows the XRPD spectrum of crystal form B of the compound of formula (I).
Figure 6:
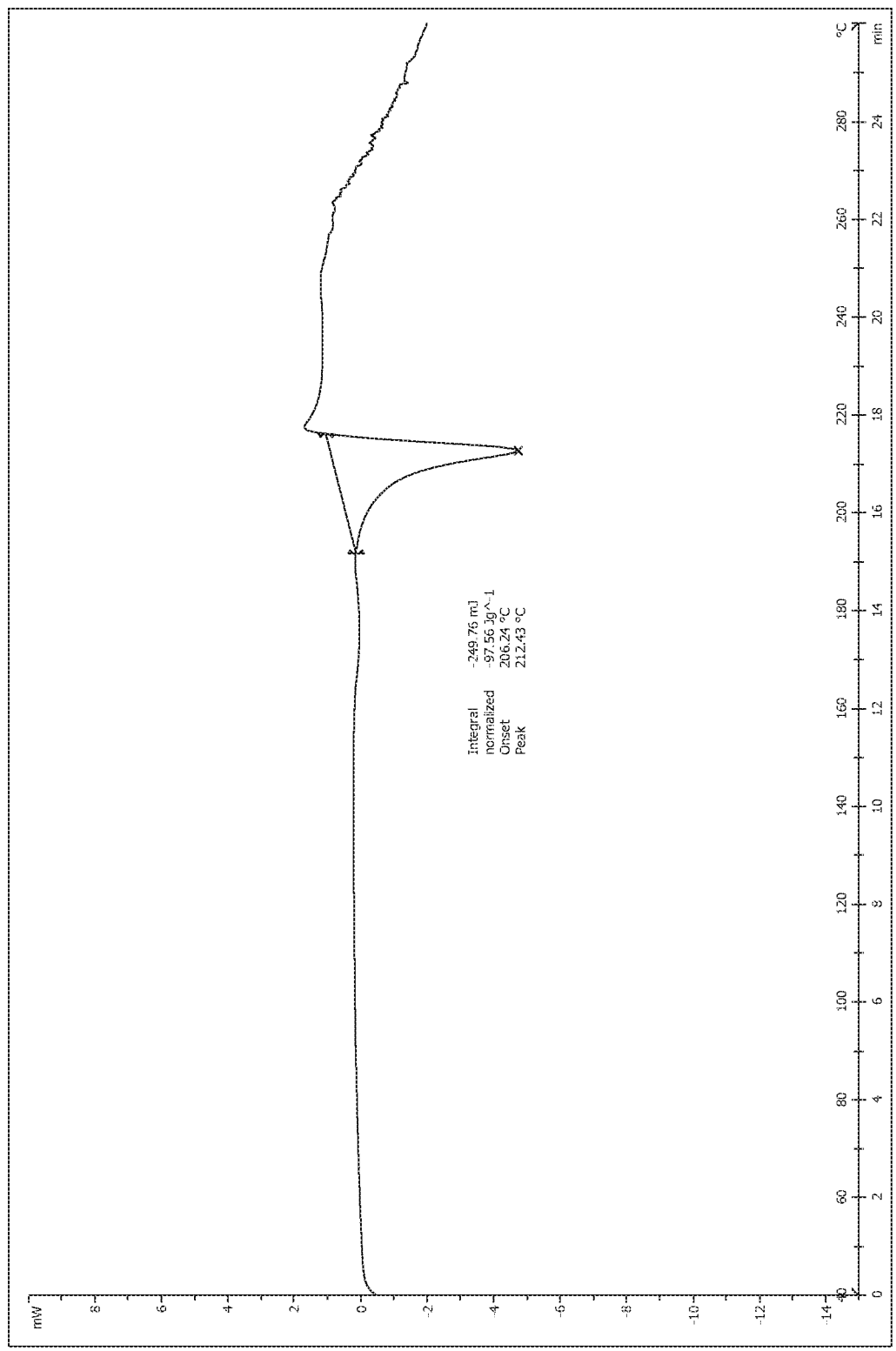
FIG. 6 shows the DSC spectrum of crystal form B of the compound of formula (I).
Figure 7:
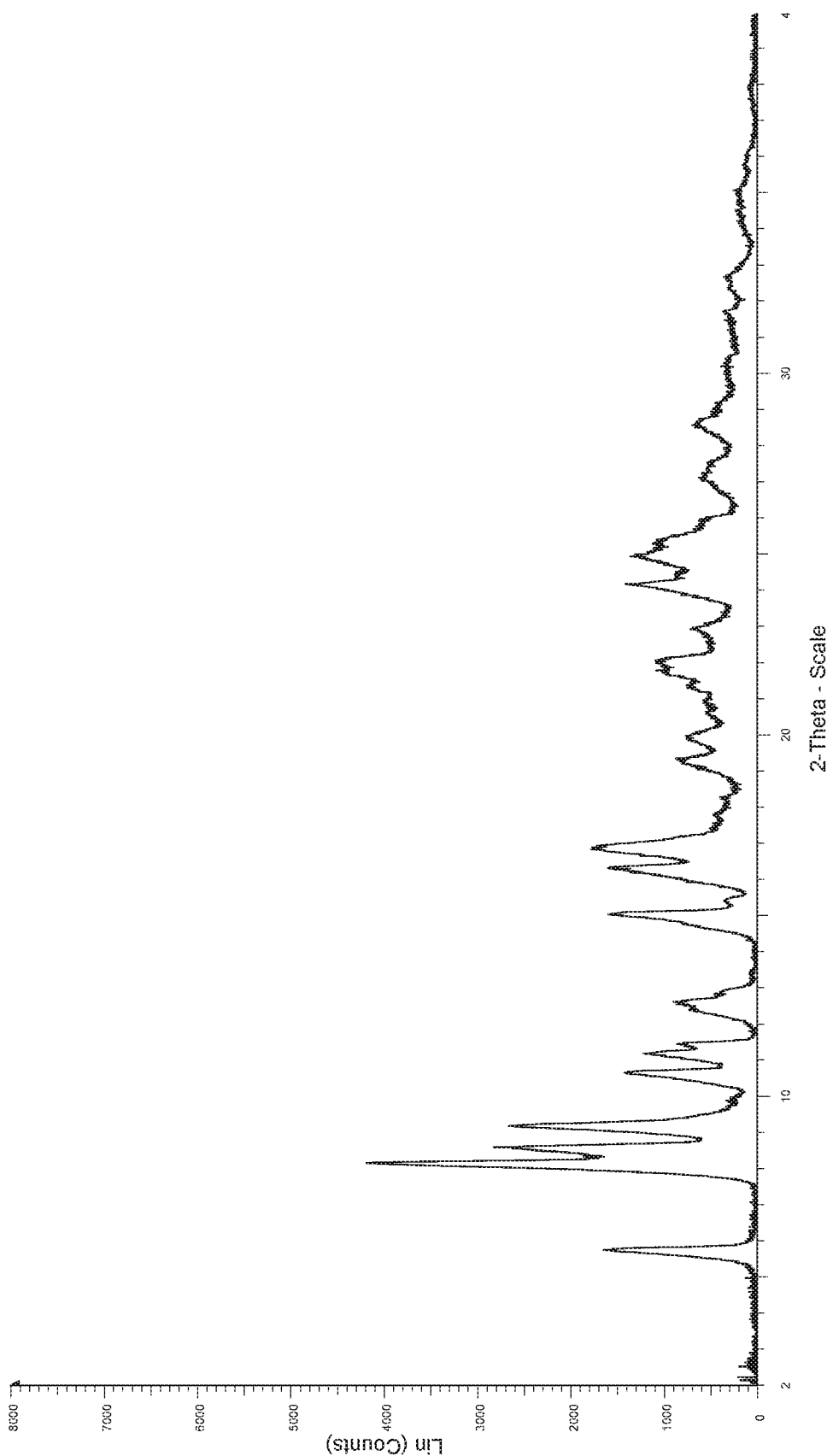
FIG. 7 shows the XRPD spectrum of crystal form C of the compound of formula (I).
Figure 8:
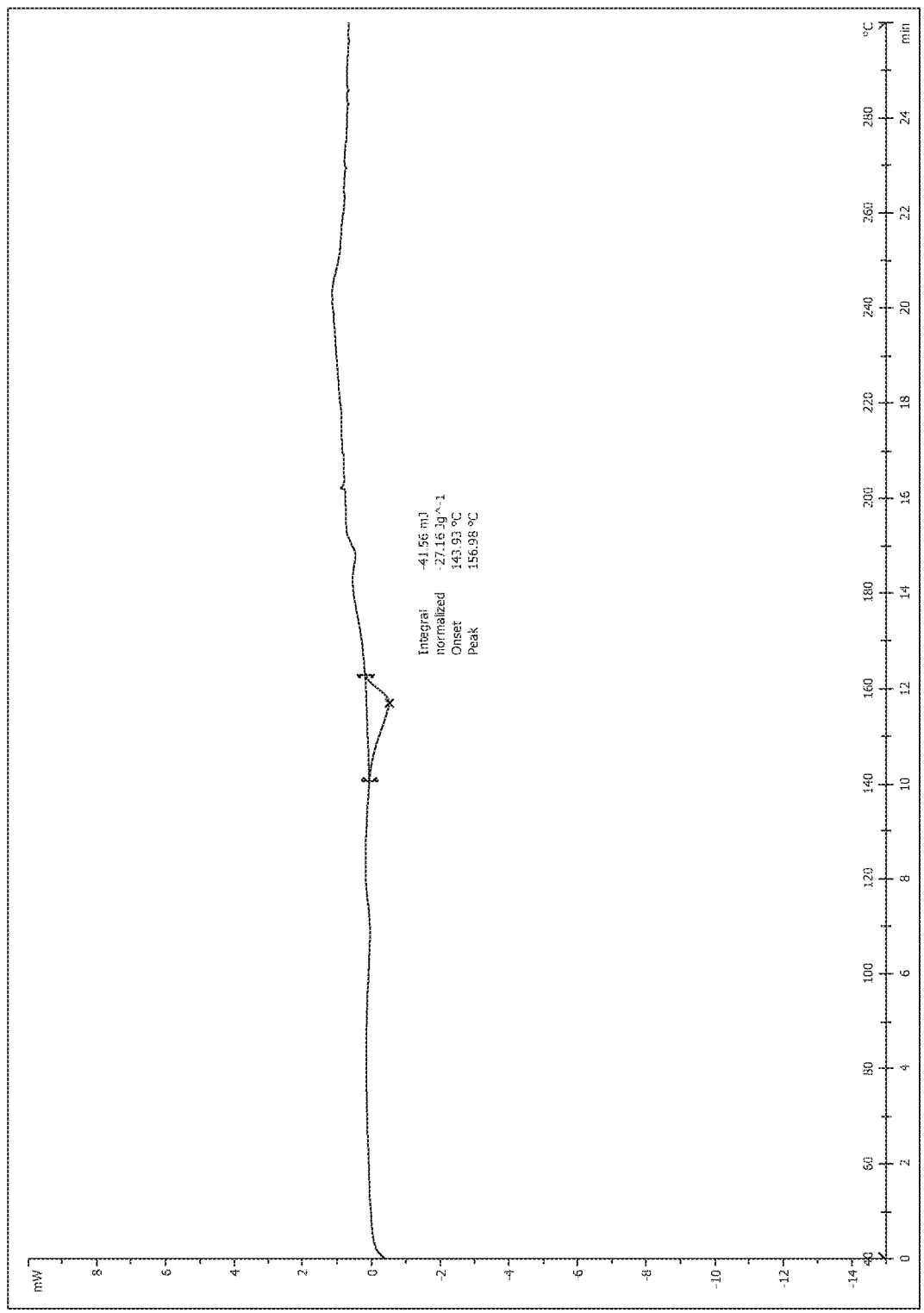
FIG. 8 shows the DSC spectrum of crystal form C of the compound of formula (I).
Figure 9:
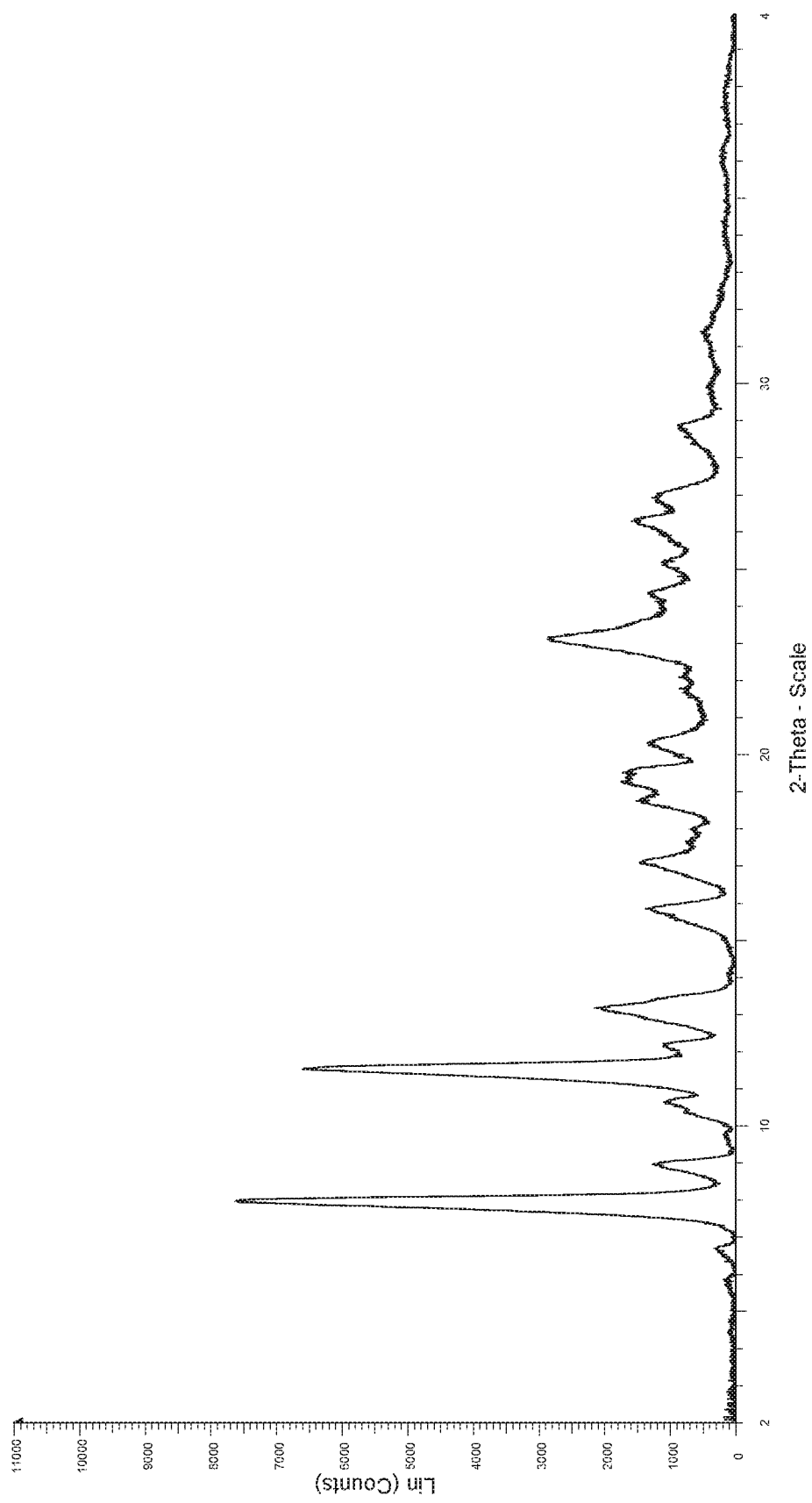
FIG. 9 shows the XRPD spectrum of crystal form D of the compound of formula (I).
Figure 10:
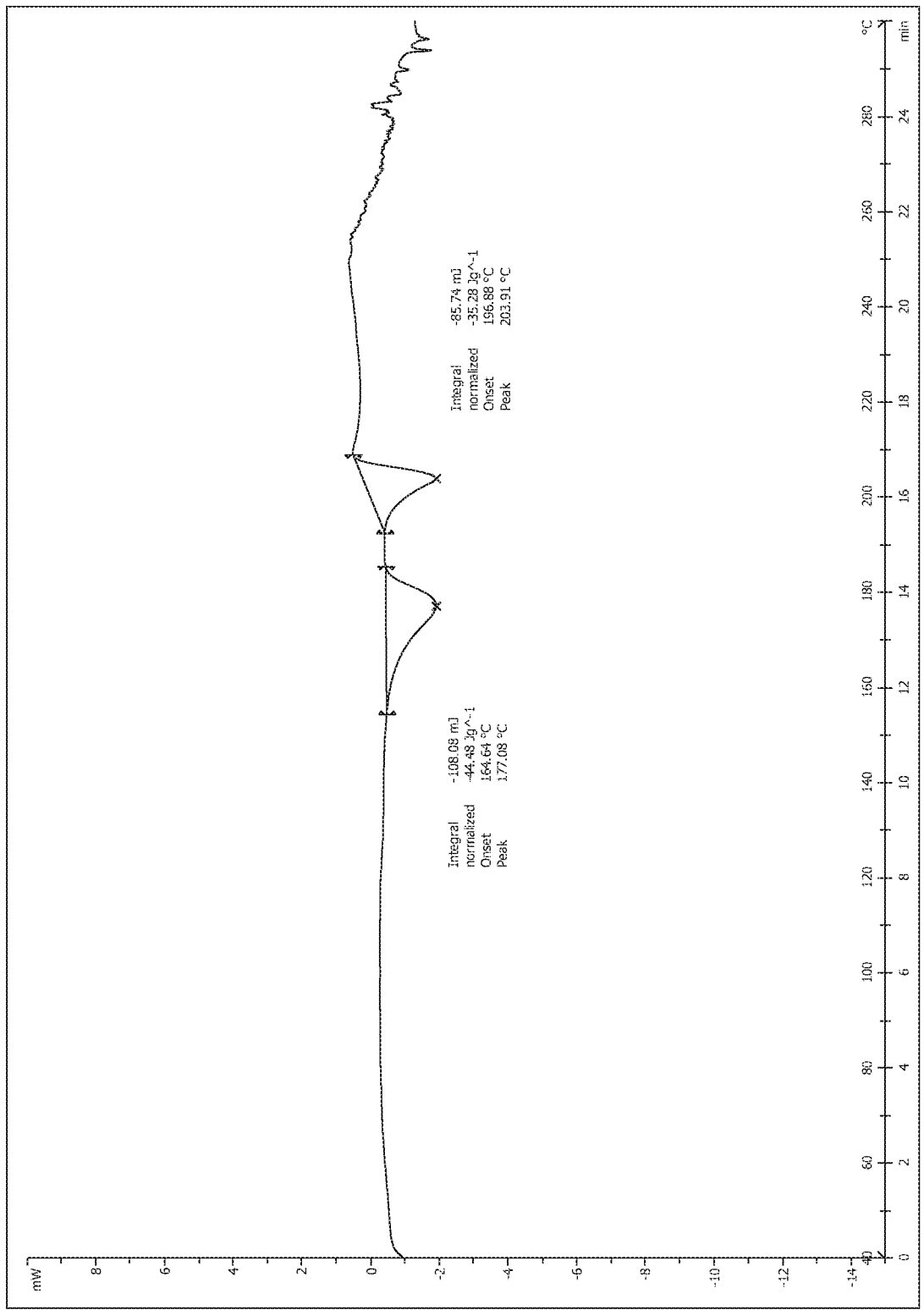
FIG. 10 shows the DSC spectrum of crystal form D of the compound of formula (I).

The crude compound of formula (I) (300 mg, 0.49 mmol) (prepared according to the method of Example 11 of WO2015062391A1) was added to a reaction flask, acetone (6 mL) was added, and the resulting mixture was stirred overnight at room temperature. The mixture was filtered and dried under vacuum to obtain 221 mg of a solid. The XRPD spectrum of the crystal sample is shown in FIG. 1. The DSC spectrum is shown in FIG. 2, in which a melting endothermic peak is at about 168.17° C., and the onset melting temperature is 154.23° C. The characteristic peaks are shown in the following table:

TABLE 1

Characteristic peaks of crystal form I

| Peak No. | 2θ [°] | d [Å] |
|---|---|---|
| Peak 1 | 5.22 | 16.92 |
| Peak 2 | 5.56 | 15.88 |
| Peak 3 | 9.15 | 9.66 |

TABLE 1-continued

Characteristic peaks of crystal form I

| Peak No. | 2θ [°] | d [Å] |
|---|---|---|
| Peak 4 | 9.79 | 9.03 |
| Peak 5 | 10.29 | 8.59 |
| Peak 6 | 11.08 | 7.98 |
| Peak 7 | 13.38 | 6.61 |
| Peak 8 | 13.81 | 6.41 |
| Peak 9 | 14.21 | 6.23 |
| Peak 10 | 14.89 | 5.94 |
| Peak 11 | 16.61 | 5.33 |
| Peak 12 | 17.19 | 5.16 |
| Peak 13 | 18.47 | 4.80 |
| Peak 14 | 19.59 | 4.53 |
| Peak 15 | 20.25 | 4.38 |
| Peak 16 | 22.16 | 4.01 |
| Peak 17 | 23.32 | 3.81 |
| Peak 18 | 24.67 | 3.61 |
| Peak 19 | 25.69 | 3.47 |
| Peak 20 | 26.72 | 3.33 |
| Peak 21 | 28.73 | 3.11 |
| Peak 22 | 29.38 | 3.04 |
| Peak 23 | 31.78 | 2.81 |
| Peak 24 | 34.02 | 2.63 |
| Peak 25 | 36.95 | 2.43 |

Example 3

The crude compound of formula (I) (500 mg, 0.82 mmol) (prepared according to the method of Example 11 of WO2015062391A1) was added to a reaction flask, methanol (50 mL) was added, and the resulting mixture was heated to reflux. The heating was stopped when the solid was dissolved, and the solution was stirred to precipitate a crystal. The mixture was filtered and dried under vacuum to obtain 350 mg of a solid. The product was identified as crystal form I after studying and comparing the XRPD and DSC spectra of the crystal sample.

Example 4

The crude compound of formula (I) (500 mg, 0.82 mmol) (prepared according to the method of Example 11 of WO2015062391A1) was added to a reaction flask, ethanol (125 mL) was added, and the resulting mixture was heated to reflux. The heating was stopped when the solid was dissolved, and the solution was stirred to precipitate a crystal. The mixture was filtered and dried under vacuum to obtain 406 mg of a solid. The product was identified as crystal form I after studying and comparing the XRPD and DSC spectra of the crystal sample.

Example 5

The crude compound of formula (I) (500 mg, 0.82 mmol) (prepared according to the method of Example 11 of WO2015062391A1) was added to a reaction flask, isopropanol (10 mL) was added, and the resulting mixture was stirred overnight at room temperature. The mixture was filtered and dried under vacuum to obtain 445 mg of a solid. The product was identified as crystal form I after studying and comparing the XRPD and DSC spectra of the crystal sample.

Example 6

The crude compound of formula (I) (500 mg, 0.82 mmol) (prepared according to the method of Example 11 of WO2015062391A1) was added to a reaction flask, acetone (25 mL) was added, and the resulting mixture was heated to reflux. The heating was stopped when the solid was dissolved, and the solution was stirred to precipitate a crystal. The mixture was filtered and dried under vacuum to obtain 251 mg of a solid. The product was identified as crystal form I after studying and comparing the XRPD and DSC spectra of the crystal sample.

Example 7

The crude compound of formula (I) (300 mg, 0.49 mmol) (prepared according to the method of Example 11 of WO2015062391A1) was added to a reaction flask, ethyl acetate (9 mL) was added, and the resulting mixture was stirred overnight at room temperature. The mixture was filtered and dried under vacuum to obtain 224 mg of a solid. The product was identified as crystal form I after studying and comparing the XRPD and DSC spectra of the crystal sample.

Example 8

The crude compound of formula (I) (300 mg, 0.49 mmol) (prepared according to the method of Example 11 of WO2015062391A1) was added to a reaction flask, tetrahydrofuran/ethanol (8 mL, V:V=1:1) was added, and the resulting mixture was heated to reflux. The heating was stopped when the solid was dissolved, and the solution was stirred to precipitate a crystal. The mixture was filtered and dried under vacuum to obtain 197 mg of a solid. The product was identified as crystal form I after studying and comparing the XRPD and DSC spectra of the crystal sample.

Example 9

The crude compound of formula (I) (300 mg, 0.49 mmol) (prepared according to the method of Example 11 of WO2015062391A1) was added to a reaction flask, tetrahydrofuran/isopropanol (12 mL, V:V=1:1) was added, and the resulting mixture was heated to reflux. The heating was stopped when the solid was dissolved, and the solution was stirred to precipitate a crystal. The mixture was filtered and dried under vacuum to obtain 182 mg of a solid. The product was identified as crystal form I after studying and comparing the XRPD and DSC spectra of the crystal sample.

Example 10

The crude compound of formula (I) (300 mg, 0.49 mmol) (prepared according to the method of Example 11 of WO2015062391A1) was added to a reaction flask, methanol (6 mL) was added, and the resulting mixture was stirred overnight at room temperature. The mixture was filtered and dried under vacuum to obtain 239 mg of a solid. The product was identified as crystal form I after studying and comparing the XRPD and DSC spectra of the crystal sample.

Example 11

The crude compound of formula (I) (300 mg, 0.49 mmol) (prepared according to the method of Example 11 of WO2015062391A1) was added to a reaction flask, ethanol (6 mL) was added, and the resulting mixture was stirred overnight at room temperature. The mixture was filtered and dried under vacuum to obtain 231 mg of a solid. The product was identified as crystal form I after studying and comparing the XRPD and DSC spectra of the crystal sample.

Example 12

1-(4-(7-(2,6-Difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxy urea (500 mg, 0.82 mmol) (prepared according to Example 1) was added to a reaction flask, purified water (10 mL) was added, and the resulting mixture was pulped for 5 hours at room temperature. The mixture was filtered and dried to obtain 369 mg of a solid. The crystal form was identified as crystal form A by XRPD and DSC spectra.

The resulting crystal form A was added to a reaction flask, ethanol (4 mL) was added, and the mixture was stirred overnight at room temperature. The mixture was filtered and dried under vacuum to obtain 89 mg of a solid. The product was identified as crystal form I after studying and comparing the XRPD and DSC spectra of the crystal sample.

Example 13

1-(4-(7-(2,6-Difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxy urea (300 mg, 0.49 mmol) (prepared according to Example 1) was added to a reaction flask, acetonitrile (9 mL) was added, and the resulting mixture was heated to reflux. The heating was stopped when the solid was dissolved completely, and the solution was cooled to precipitate a crystal. The mixture was filtered and dried to obtain 243 mg of a solid. The crystal form was identified as crystal form B by XRPD and DSC spectra.

The resulting crystal form B was added to a reaction flask, ethanol (4 mL) was added, and the mixture was stirred overnight at room temperature. The mixture was filtered and dried under vacuum to obtain 80 mg of a solid. The product was identified as crystal form I after studying and comparing the XRPD and DSC spectra of the crystal sample.

Example 14

1-(4-(7-(2,6-Difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxy urea (300 mg, 0.49 mmol) (prepared according to Example 1) was added to a reaction flask, 1,4-dioxane (15 mL) was added, and the resulting mixture was heated to reflux. The heating was stopped when the solid was dissolved completely, and the solution was cooled to precipitate a crystal. The mixture was filtered and dried to obtain 205 mg of a solid. The crystal form was identified as crystal form C by XRPD and DSC spectra.

The resulting crystal form C was added to a reaction flask, ethanol (10 mL) was added, and the mixture was stirred overnight at room temperature. The mixture was filtered and dried under vacuum to obtain 78 mg of a solid (yield: 78.0%). The product was identified as crystal form I after studying and comparing the XRPD and DSC spectra of the crystal sample.

Example 15

1-(4-(7-(2,6-Difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxy urea (300 mg, 0.49 mmol) (prepared according to Example 1) was added to a reaction flask, tetrahydrofuran/water (15 mL, V:V=1:1) was added, and the resulting mixture was heated to reflux. The heating was stopped when the solid was dissolved completely, and the solution was cooled to precipitate a crystal. The mixture was filtered and dried to obtain 205 mg of a solid. The crystal form was identified as crystal form D by XRPD and DSC spectra.

The resulting crystal form D was added to a reaction flask, ethanol (10 mL) was added, and the mixture was stirred overnight at room temperature. The mixture was filtered and dried under vacuum to obtain 78 mg of a solid. The product was identified as crystal form I after studying and comparing the XRPD and DSC spectra of the crystal sample.

Example 16

The product sample of crystal form I prepared in Example 1 and the product samples of crystal forms A, B, C and D prepared in Examples 12, 13, 14 and 15 were spread flat in the air to test sample stability under conditions of lighting (4500 Lux), heating (40° C., 60° C.), and high humidity (RH 75%, RH 90%). Samplings were carried out on Day 5 and Day 10. The purity as detected by HPLC is shown in Table 2.

Test Results:

TABLE 2

Stability comparison of crystal form I of the compound of formula (I) of the present invention and crystal forms A, B, C and D of the compound of formula (I)

| Batch number | Time (day) | Lighting | 40° C. | 60° C. | RH 75% | RH 90% |
| --- | --- | --- | --- | --- | --- | --- |
| Crystal form I | 0 | 99.36% | 99.36% | 99.36% | 99.36% | 99.36% |
|  | 5 | 99.26% | 99.33% | 99.24% | 99.22% | 99.27% |
|  | 10 | 99.20% | 99.41% | 99.30% | 99.31% | 99.27% |
| Crystal form A | 0 | 97.86% | 97.86% | 97.86% | 97.86% | 97.86% |
|  | 5 | 97.27% | 97.50% | 97.62% | 97.61% | 97.59% |
|  | 10 | 97.13% | 97.52% | 97.50% | 97.65% | 97.79% |
| Crystal form B | 0 | 99.69% | 99.69% | 99.69% | 99.69% | 99.69% |
|  | 5 | 99.39% | 99.45% | 99.45% | 99.52% | 99.47% |
|  | 10 | 99.19% | 99.03% | 99.34% | 99.34% | 99.34% |
| Crystal form C | 0 | 99.75% | 99.75% | 99.75% | 99.75% | 99.75% |
|  | 5 | 98.30% | 99.57% | 99.53% | 99.51% | 99.54% |
|  | 10 | 96.83% | 99.35% | 99.47% | 99.48% | 99.38% |
| Crystal form D | 0 | 99.67% | 99.67% | 99.67% | 99.67% | 99.67% |
|  | 5 | 99.43% | 99.44% | 99.48% | 99.57% | 99.57% |
|  | 10 | 99.22% | 99.31% | 99.40% | 99.34% | 99.39% |

Test Conclusion

The results of the stability test in Table 2 showed that:

When being spread in the air under conditions of lighting, high humidity and high temperature, the decrease of HPLC purity data of crystal form I of the compound of formula (I) were less than that of crystal forms A, B, C and D, and the crystal form was not changed by XRPD test, indicating that the stability of crystal form I of the present invention is significantly better than that of crystal forms A, B, C and D.

Example 17

The sample of crystal form I of the compound of formula (I) prepared according to the method of Example 1 was ground, heated and tabletted. The results of crystal form stability, XRPD test and DSC test of the sample are shown in Table 3.

Test Results:

TABLE 3

Special stability study of crystal form I of the compound of formula (I)

| Sample | Treatment Process | Experimental procedure | XRPD test | DSC peak |
|---|---|---|---|---|
| Crystal form I | Grinding treatment for 10 minutes | 1 g of the sample of crystal form I of the compound of formula (I) was ground for 10 minutes in a mortar under nitrogen atmosphere. | Crystal form I | 166.16° C. |
| Crystal form I | Heating treatment for 3 hours at 80° C. | 1 g of the sample of crystal form I of the compound of formula (I) was spread flat and heated at 80° C. for 3 hours. | Crystal form I | 168.36° C. |
| Crystal form I | Tableting treatment | The sample of crystal form I of the compound of formula (I) was tableted. | Crystal form I | 168.97° C. |

Test Conclusion:

The results of the stability study in Table 3 showed that the crystal form was not changed during the grinding, heating and tableting procedure, indicating that the crystal form I of the present invention is stable.

What is claimed is:

1. Crystal form I of a compound of formula (I), characterized by an X-ray powder diffraction spectrum comprising diffraction peaks at diffraction angles 2θ±0.2 of 5.56, 9.15, 9.79, 11.08, 19.59, 20.25 and 22.16:

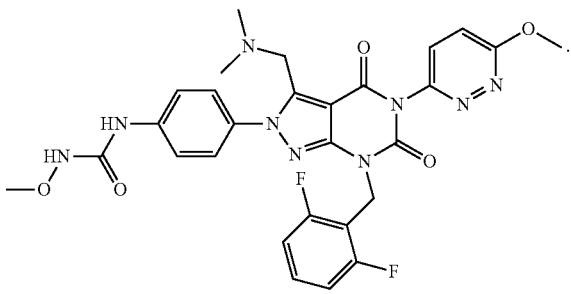

(I)

2. The crystal form I according to claim 1, wherein the X-ray powder diffraction spectrum comprises diffraction peaks at diffraction angles 2θ±0.2 of 5.56, 9.15, 9.79, 10.29, 11.08, 14.21, 16.61, 19.59, 20.25, 22.16 and 25.69.

3. The crystal form I according to claim 2, wherein the X-ray powder diffraction spectrum comprises diffraction peaks at diffraction angles 2θ±0.2 of 5.22, 5.56, 9.15, 9.79, 10.29, 11.08, 13.38, 13.81, 14.21, 14.89, 16.61, 17.19, 18.47, 19.59, 20.25, 22.16, 23.32, 24.67, 25.69, 26.72, 28.73, 29.38, 31.78, 34.02 and 36.95.

4. A method for preparing the crystal form I of the compound of formula (I) according to claim 1, comprising dissolving the compound of formula (I) in an organic solvent to precipitate a crystal, filtering, washing and drying the crystal to obtain the desired crystal form I, wherein the organic solvent is selected from the group consisting of an alcohol, ketone, ester, ether, a mixed solvent of an ether and an alcohol, and a mixed solvent of a ketone and water; and the alcohol solvent is selected from the group consisting of methanol, ethanol and isopropanol.

5. The crystal form I according to claim 1, characterized by a DSC spectrum comprising a melting endothermic peak of 160° C. to 175° C.

6. A pharmaceutical composition comprising the crystal form I according to claim 1, and one or more pharmaceutically acceptable carriers, diluents or excipients.

7. A method for preparing the crystal form I of the compound of formula (I) according to claim 1, comprising adding the compound of formula (I) into an organic solvent to obtain a mixture; pulping the mixture; and filtering, washing and drying a crystal to obtain the desired crystal form I, wherein the organic solvent is selected from the group consisting of an alcohol, ketone, ester, ether, a mixed solvent of an ether and an alcohol, and a mixed solvent of a ketone and water; and the alcohol solvent is selected from the group consisting of methanol, ethanol, and isopropanol.

8. The method according to claim 4, wherein the ketone solvent is acetone.

9. The method according to claim 4, wherein the ester solvent is ethyl acetate.

10. The method according to claim 4, wherein the ether solvent is tetrahydrofuran.

11. The method according to claim 4, wherein the mixed solvent of the ether and the alcohol is tetrahydrofuran/ethanol or tetrahydrofuran/isopropanol.

12. The method according to claim 4, wherein the mixed solvent of the ketone and water is acetone/water.

13. The method according to claim 7, wherein the ketone solvent is acetone.

14. The method according to claim 7, wherein the ester solvent is ethyl acetate.

15. The method according to claim 7, wherein the ether solvent is tetrahydrofuran.

16. The method according to claim 7, wherein the mixed solvent of the ether and the alcohol is tetrahydrofuran/ethanol or tetrahydrofuran/isopropanol.

17. The method according to claim 7, wherein the mixed solvent of the ketone and water is acetone/water.

18. The crystal form I according to claim 5, wherein the DSC spectrum comprises a melting endothermic peak of from 165° C. to 170° C.

19. The crystal form I according to claim 5, wherein the DSC spectrum comprises a melting endothermic peak of 168.71° C.

20. A method for treating a disease associated with GnRH receptor antagonist, comprising administering to a subject in need thereof an effective amount of the pharmaceutical composition according to claim 6, wherein the disease is selected from the group consisting of endometriosis, uterine leiomyoma, and prostate cancer.

* * * * *